United States Patent
Wang

(10) Patent No.: US 9,725,482 B2
(45) Date of Patent: Aug. 8, 2017

(54) PENTACYCLIC TRITERPENOID COMPOUND WITH MODIFIED STRUCTURE AND PREPARATION METHOD AND USE THEREOF

(71) Applicant: Suzhou Botany Biomedicals Co., Ltd, Suzhou, Jiangshu (CN)

(72) Inventor: Honglin Wang, Shanghai (CN)

(73) Assignee: Suzhou Botany Biomedical Co., Ltd., Suzhou, Jiangshu (CN)

(*) Notice: Subject to any disclaimer, the term of this patent is extended or adjusted under 35 U.S.C. 154(b) by 0 days.

(21) Appl. No.: 15/100,076

(22) PCT Filed: Nov. 18, 2014

(86) PCT No.: PCT/CN2014/091371
§ 371 (c)(1),
(2) Date: May 27, 2016

(87) PCT Pub. No.: WO2015/078321
PCT Pub. Date: Jun. 4, 2015

(65) Prior Publication Data
US 2017/0002039 A1  Jan. 5, 2017

(30) Foreign Application Priority Data
Nov. 30, 2013 (CN) .......................... 2013 1 0623314

(51) Int. Cl.
*C07J 63/00* (2006.01)

(52) U.S. Cl.
CPC .................................. *C07J 63/008* (2013.01)

(58) Field of Classification Search
None
See application file for complete search history.

(56) References Cited

U.S. PATENT DOCUMENTS

2012/0035176 A1    2/2012  Gokaraju et al.

FOREIGN PATENT DOCUMENTS

| CN | 101724004 | 6/2010 |
| CN | 101775058 | 7/2010 |

OTHER PUBLICATIONS

Kumar et al., "Acyl derivatives of boswellic acids as inhibitors of NF-kB and STATs", Biorganic & Medicinal Chemistry Letters 22 (2012) 431-435.
International Search Report in PCT/CN2014/091371 mailed Feb. 13, 2015.

*Primary Examiner* — Bong-Sook Baek
(74) *Attorney, Agent, or Firm* — Greenberg Traurig, LLP; Fang Xie

(57) ABSTRACT

The present invention relates to new pentacyclic triterpenes, their preparation method and use. The compounds of the present invention could effectively treat psoriasis and selectively inhibit in vitro differentiation of the $T_H1$ and $T_H17$ cells, thereby could be used to treat the $T_H1$- or $T_H17$-mediated autoimmune diseases.

12 Claims, 7 Drawing Sheets

PENTACYCLIC TRITERPENOID COMPOUND WITH MODIFIED STRUCTURE AND PREPARATION METHOD AND USE THEREOF

CROSS REFERENCE TO RELATED APPLICATIONS

This application is a national phase filing under 35 U.S.C. 371 of International Application No. PCT/CN2014/091371, filed Nov. 18, 2014, which claims priority to and the benefit of Chinese Patent Application No. CN 201310623314.2, filed Nov. 30, 2013, the disclosures of both of which are incorporated herein by reference in their entireties.

TECHNICAL FIELD

The present invention belongs to the field of medicine. More specifically, the present invention relates to new compounds for use in treatment of psoriasis.

TECHNICAL BACKGROUND

Psoriasis, also called as "lepra alphos", is a common chronic, recrudescent, inflammatory skin disease, characterized in that multiple layers of silvery white, dry scales occur repeatedly on erythema. In the Chinese traditional medicine it is called "Baibi". It is also called "Songpi Xian" in ancient medical books. In the western medicine, it is called psoriasis. Psoriasis usually occurs in scalp, extensor aspect of arms and legs, and on the back. Psoriasis relapses or becomes worse in spring and winter while relieves in summer and autumn. Psoriasis is one of the ten recurring illnesses as listed by WHO, having a morbidity of about 2-3% in Europe and USA (Schoen and Boehncke, N Engl J Med, 2005). In China, according to incomplete statistics, the incidence of psoriasis is about 0.5%, and there are about 7 million of patients suffering from psoriasis. Psoriasis mainly occurs in young adults of 25 to 45 years old, accounting for about 81%. Recently, children's incidence is increasing. Psoriasis is difficult to be cured and readily occurs repeatedly, thus it not only causes physical pain but also causes a huge psychological burden for the patients and seriously affect their life quality. As a result, psoriasis is one of the important research subjects in the field of skin disorders in the world.

Treatment of psoriasis is expensive in the world, especially in the case of using the expensive biological drugs. Therefore, it is an urgent need to develop drugs with low price and good safety for treating psoriasis. The research results made by the present inventors show that the nucleic acid transcription factor, NF-kappa B, is over activated in epidermis and dermis of the patients with psoriasis as compared to the skin of a normal person, which leads to a great release of the inflammatory factors, such as TNF-alpha, IL-17 and IL-23 etc. Excessive amounts of inflammatory factors, such as TNF-alpha, IL-17 and IL-23, induce human psoriasis (Wang et al., J Immunol, 2009).

One of the drugs currently used for treating psoriasis approved by FDA, etanercept, is a bio-agent, which is an inhibitor of tumor necrosis factor. Etanercept is a humanized antibody for blocking the receptor of the tumor necrosis factor. Since the tumor necrosis factor is essential in the normal immune response in organism, the humanized antibody non-selectively blocks the tumor necrosis factor, resulting in side effects after administration or even easy to recurrence after stopping administration. Moreover, since it is an antibody, it has a high production cost and thus it is expensive, the ordinary patients are difficult to afford expenses for drugs. Additionally, ustekinumab, which is a monoclonal antibody against IL-23, clinically exhibits a very well treatment effect on psoriasis. But it has a high production cost and an expensive price.

Acetyl-11-keto-β-boswellic acid (AKBA) is one of the important components of the colloidal resin, frankincense, from *Boswellia carterii Birdw*. Concentration and purification of AKBA from natural mastic tree extract has been described in WO 03/0746, US 20030199581 and WO 03/077860. Product with high purity may be obtained via chromatography separation and re-crystallization. Frankincense extract has been used as an anti-inflammatory agent in the traditional medicine for treating patients suffering from, such as arthritis and ulcerative colitis. Additionally, boswellic acid is also noticeable due to their anti-proliferative property. Boswellic acid can inhibit several leukaemia cell lines, growth of melanoma and death of cells in vitro. Study on boswellic acid shows that acetyl-11-keto-β-boswellic acid exhibits the most obvious 5-LOX inhibitory activity (Sailer et al., British J Pharmacology, 1996). AKBA has a structure as set forth below:

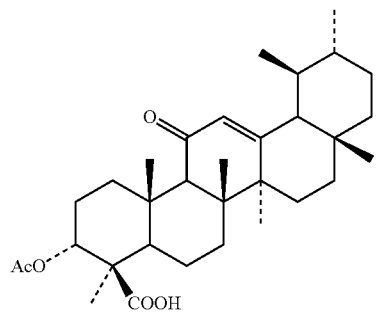

The present inventors have been working on the pathogenesis and treatment of psoriasis for many years. Molecular immunological mechanism of AKBA in treating psoriasis has been clarified by using a mouse model for psoriasis by the present inventors. The research results were published on October 2009 in The Journal of Immunology (Wang et al., J Immunol, 2009). The innovative research results have been highly concerned by the international counterparts after its publication and were reported by Nature Reviews Rheumatology, one of the international authoritative magazines, as a research highlight.

Generally speaking, the existing drugs for treating psoriasis have a high production cost and poor targeting property. Acetyl-11-keto-β-boswellic acid can be used to treat psoriasis but it still needs to be further modified to greatly improve the treatment effect.

SUMMARY OF INVENTION

The present disclosure is intended to provide new compounds, preparation method and use thereof.

In the first aspect of the present disclosure, a compound of formula (I), or isomer, solvate or precursor or pharmaceutically acceptable salt thereof is provided:

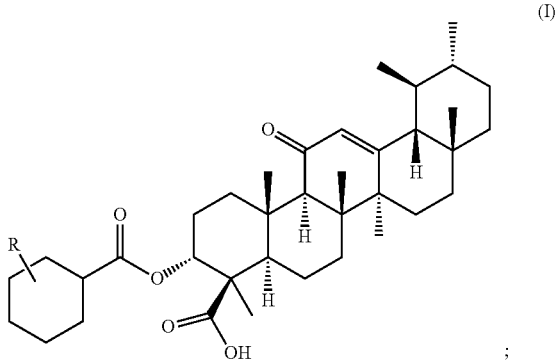

wherein R is independently selected from the group consisting of H, OH, C1-C4 alkyl, C2-C4 alkenyl, C2-X4 alkynyl and halogen.

In one preferred embodiment, R of the compound of formula (I) is independently selected from the group consisting of H, OH and C1-C2 alkyl.

In one preferred embodiment, R of the compound of formula (I) is H.

In another aspect of the present disclosure, a method for preparing the compound of formula (I) is provided:

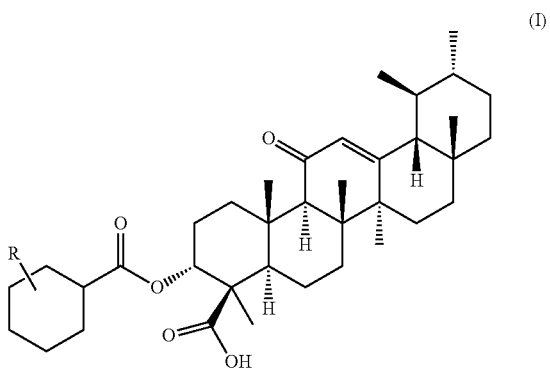

wherein the method comprises replacing the AcO group of the starting material, acetyl-11-keto-β-boswellic acid, with the following group:

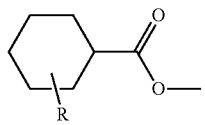

In one preferred embodiment, the method comprises the following steps:

(i) reacting the starting material, acetyl-11-keto-β-boswellic acid, with a base to produce 11-keto-β-boswellic acid; and (ii) reacting the 11-keto-β-boswellic acid with cyclohexanecarboxylic acid chloride to produce the compound of formula (I).

The base includes but is not limited to an organic base, such as triethylamine, tributylamine, N-methyl morpholine, N,N-diisopropylethylamine, N-Methylpyrrolidine, pyridine, 4-(N,N-dimethylamino)pyridine, morpholine, imidazole, 2-methylimizole, 4-methylimizole, etc; an inorganic base, such as alkali metal hydrides, such as sodium hydride and potassium hydride, etc.; sodium amide; n-butyllithium; lithium diisopropylamide; alkali metal hydroxide, such as lithium hydroxide, sodium hydroxide, potassium hydroxide and cesium hydroxide; alkaline earth metal hydroxide, such as aluminum hydroxide, magnesium hydroxide, calcium hydroxide, etc.; alkali metal carbonate, such as sodium carbonate, potassium carbonate, lithium carbonate, cesium carbonate, etc.; alkali-earth metal's carbonate, such as magnesium carbonate, calcium carbonate, etc.; alkali metal bicarbonate, such as sodium bicarbonate, potassium bicarbonate, etc.; ion exchange resin, including resin bound by ions, such as sodium ion, potassium ion, lithium ion, calcium ion, magnesium ion, substituted or unsubstituted ammonium ion, etc.; and other suitable bases.

In another preferred embodiment, step (i) in the method comprises adding acetyl-11-keto-β-boswellic acid (AKBA) and potassium hydroxide (KOH) into a two-neck flask; adding isopropanol as a solvent under nitrogen protection; refluxing while heating; evaporating the solvent with rotary evaporator to produce a white solid; adding dichloromethane and then diluted hydrochloric acid to adjust the pH value of the mixed system to be acidic; extracting the water phase by dichloromethane, collecting the dichloromethane solvent and drying with anhydrous magnesium sulfate; evaporating the solvent to produce a brown oily product; purifying the brown oily product by column chromatography by using petroleum ether:ethyl acetate as an eluant to obtain KBA (acetyl-11-keto-β-boswellic acid), which is a white solid; step (ii) comprises dissolving KBA in dichloromethane containing 4-dimethylpyridine, adding triethylamine and cyclohexanecarboxylic acid chloride un-substituted or substituted at the cyclohexyl group, and placing in an ice bath overnight; treating the reaction mixture with sodium bicarbonate after completion of the reaction; extracting by dichloromethane; collecting the dichloromethane solvent and drying the mixture with anhydrous magnesium sulfate; evaporating the solvent to produce a white solid; purifying the white solid by column chromatography by using petroleum ether:ethyl acetate as an eluant to obtain the acetylated product 3-o-α-cyclohexanoyl-11-keto-β-boswellic acid.

In another aspect of the present disclosure, use of the compound of formula (I), or isomer, solvate or precursor or pharmaceutically acceptable salt thereof in the manufacture of a medicament for treating $T_H1$- or $T_H17$-mediated autoimmune diseases.

In another aspect of the present disclosure, use of the compound of formula (I), or isomer, solvate or precursor or pharmaceutically acceptable salt thereof in the manufacture of a medicament for treating psoriasis.

In another aspect of the present disclosure, a pharmaceutical composition for treating $T_H1$- or $T_H17$-mediated autoimmune diseases or psoriasis is provided, which comprises a compound of formula (I), or isomer, solvate or precursor or a pharmaceutically acceptable salt thereof, and a pharmaceutically acceptable carrier.

In one preferred embodiment, the compound of formula (I), or isomer, solvate or precursor or a pharmaceutically acceptable salt thereof is present in the pharmaceutical composition in an effective amount. Preferably, the effective amount is 0.01-5 wt %, more preferably 0.03-3 wt %, further more preferably 0.05-1 wt %.

In another preferred embodiment, the pharmaceutical composition is a topical formulation. Preferably, the pharmaceutically acceptable carrier includes glycerol, propylene glycol, Carbomer or triethanolamine.

In another preferred embodiment, the pH value of the pharmaceutical composition is in the range of 5.5-6.5, preferably 5.8-6.0.

In another aspect of the present disclosure, a kit for treating $T_H1$- or $T_H17$-mediated autoimmune diseases or psoriasis is provided, comprising the pharmaceutical composition.

In another aspect of the present disclosure, a method for treating $T_H1$- or $T_H17$-mediated autoimmune diseases or psoriasis is provided, comprising administering a subject in need thereof an effective amount of the compound of formula (I), or isomer, solvate or precursor or a pharmaceutically acceptable salt thereof.

Other aspects of the present disclosure will be apparent to the skilled artisan in view of the contents disclosed in the subject disclosure.

SPECIFIC MODE FOR CARRYING OUT THE INVENTION

Figure 1:
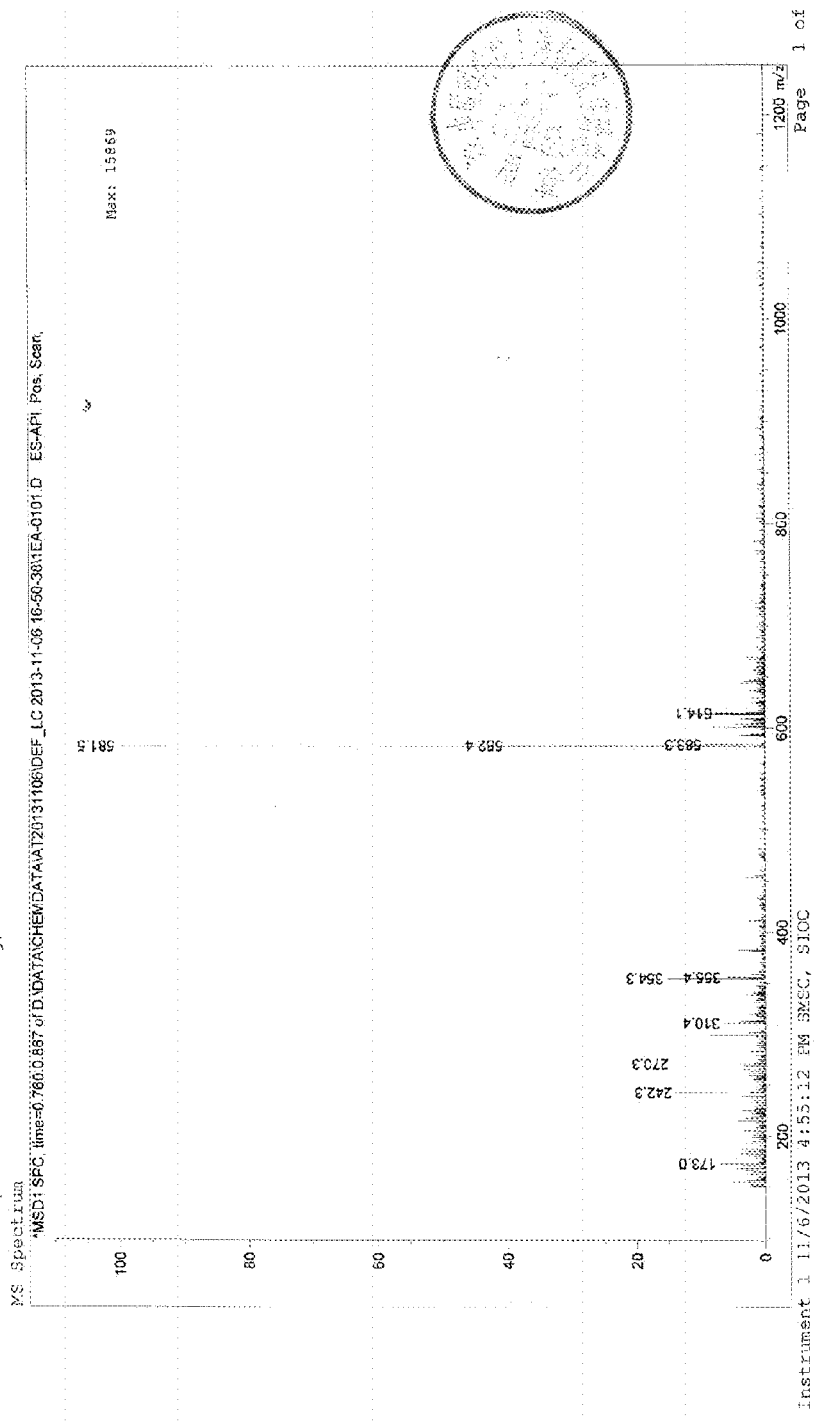
FIG. 1: Mass spectrum of the compound of formula (II).
Figure 2:
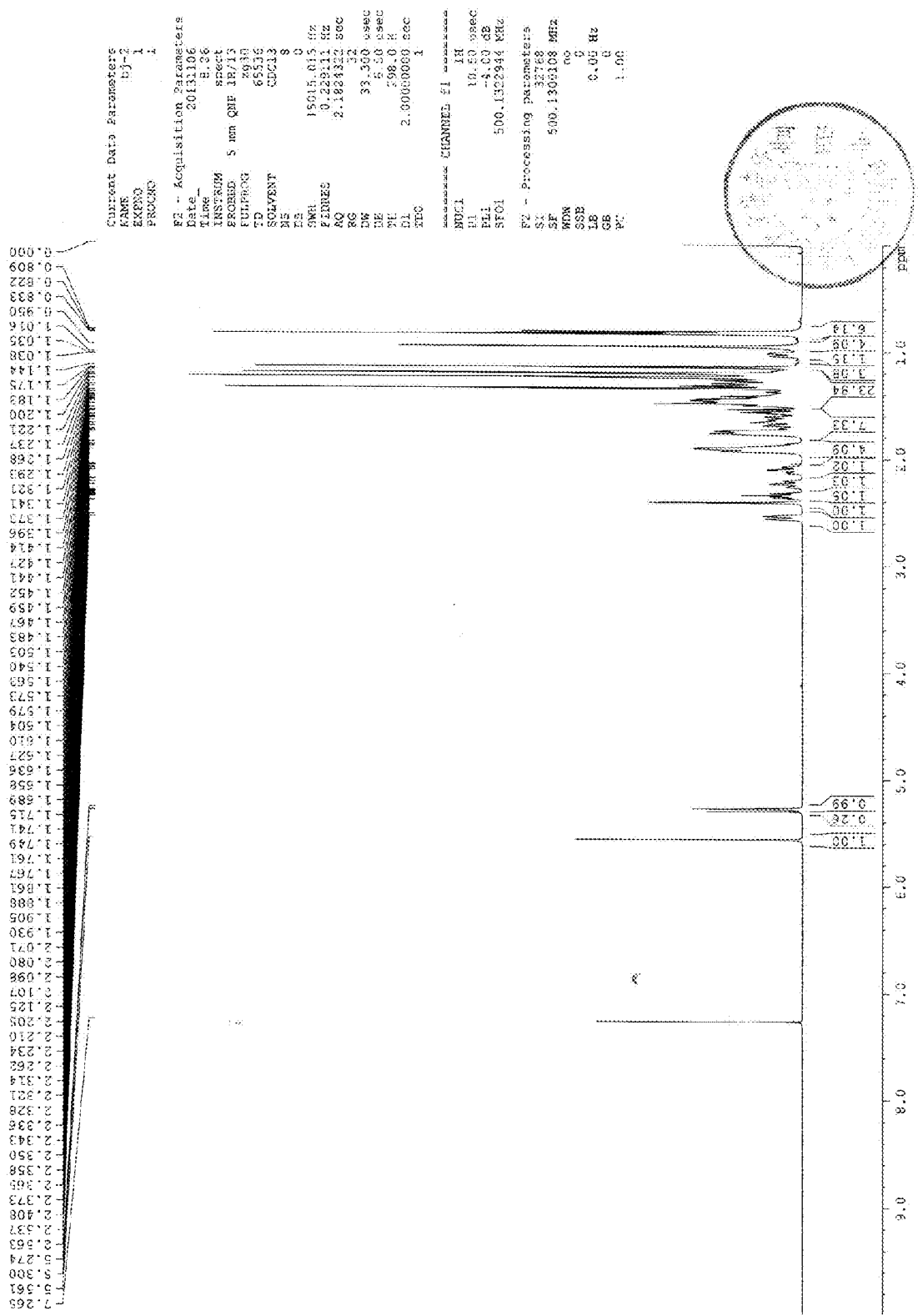
FIG. 2: Hydrogen spectrum of the compound of formula (II).
Figure 3:
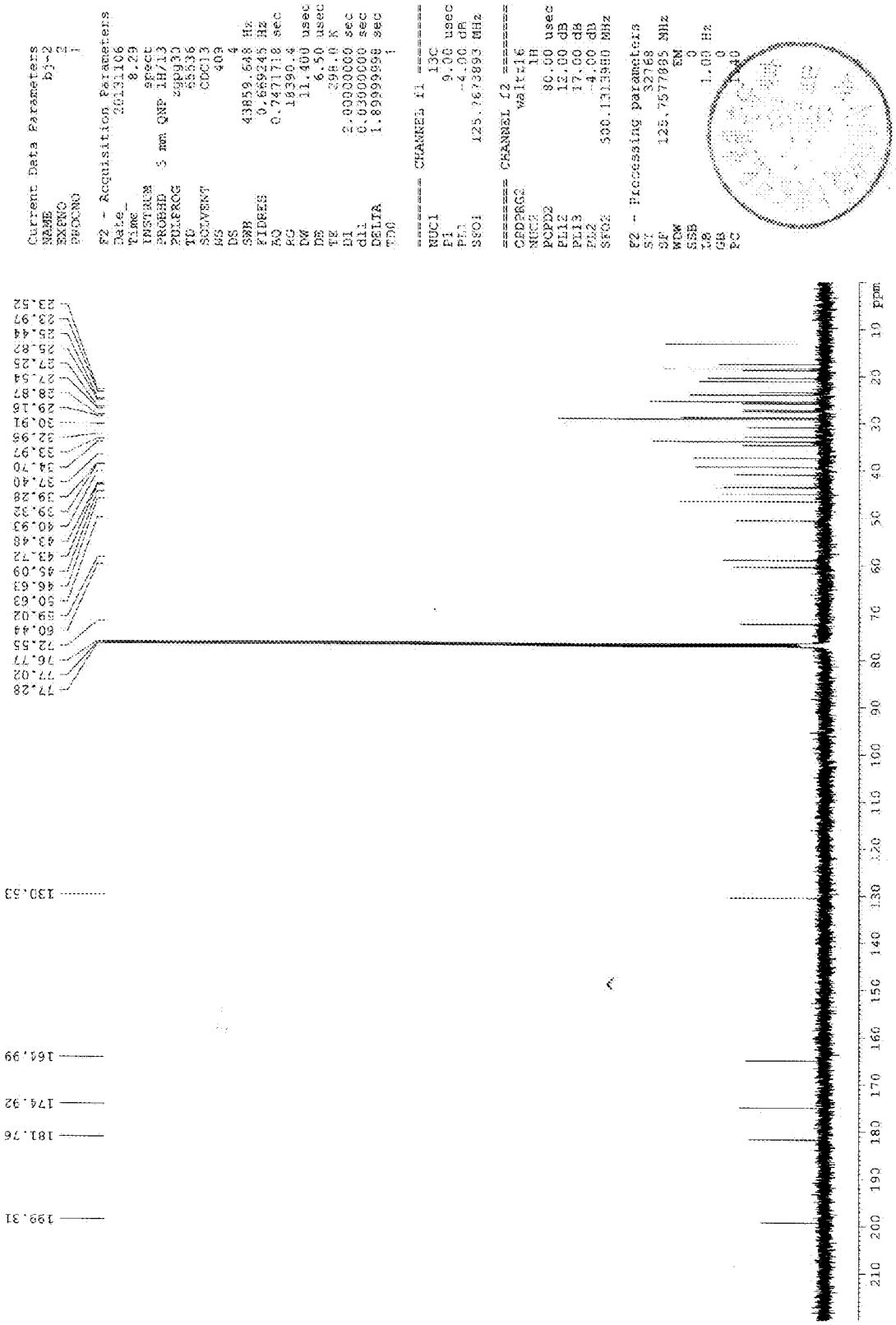
FIG. 3: Carbon spectrum of the compound of formula (II).
Figure 4:
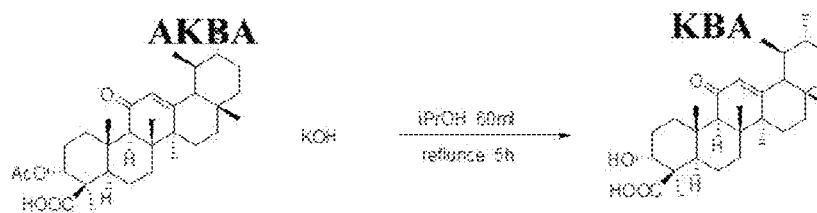
FIG. 4: Technical method and scheme of AKBA modification and preparation of the compound of formula (II).
Figure 4:
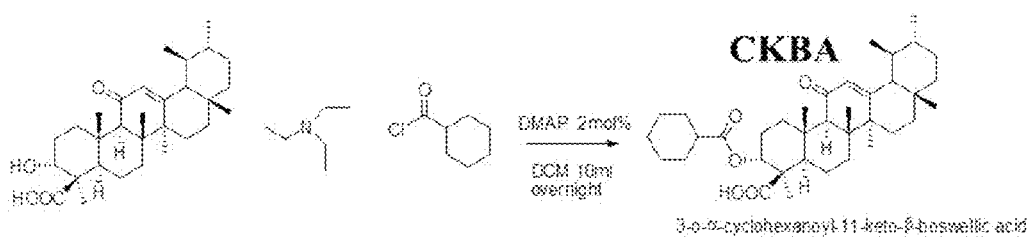

The present disclosure firstly reveals new pentacyclic triterpenes having a modified structure, which could effectively treat psoriasis, and could also selectively inhibit in vitro differentiation of the $T_H1$ and $T_H17$ cells, thereby could be used to treat the $T_H1$ or $T_H17$-mediated autoimmune diseases.

Terms

As used herein, the term "alkyl" refers to a straight or branched, saturated aliphatic hydrocarbon group containing 1-4 carbon atoms, preferably 1-2 carbon atoms. For example, alkyl includes but is not limited to methyl, ethyl, n-propyl, isopropyl, n-butyl, isobutyl, tert-butyl.

As used herein, the term "alkenyl" includes a straight or branched hydrocarbon group containing at least one carbon-carbon double bond and 2-4 carbon atoms, preferably 2-3 carbon atoms.

As used herein, the term "alkynyl" includes a straight or branched hydrocarbon group containing at least one carbon-carbon triple bond and 2-4 carbon atoms, preferably 2-3 carbon atoms.

As used herein, the term "halogen" refers to F, Cl, Br or I.

As used herein, the term "isomer" includes geometrical isomer, enantiomer, and diastereoisomer, such as cis- and trans-isomers and conformational isomer.

As used herein, the

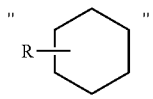

is familiar to the skilled artisan and indicates that R can be present in any one or more of the positions of the ring that can be substituted. Additionally, R may be different groups in different substation positions.

As used herein, the term "solvate" refers to the compound carrying a solvent molecule. For example, the solvate may be a hydrate.

In the present disclosure, the term "comprising" refers to that various ingredients can be used in combination in the mixture or composition of the present disclosure.

Therefore, the terms "consisting essentially of" and "consisting of" are included within the scope of the term "comprising".

In the present disclosure, the "pharmaceutically acceptable" component refers to the substance that could be used in human and/or animal without excessive adverse reaction, such as toxicity, stimulation and allergy, i.e., that exhibits a reasonable risk-to-benefit ratio.

In the present disclosure, the "pharmaceutically acceptable carrier" refers to the pharmaceutically acceptable or bromatologically acceptable solvent, suspension or excipient used to deliver the compound of formula (I), or isomer, solvate or precursor or a pharmaceutically acceptable salt thereof to an animal or human being. Carrier can be a liquid or a solid.

Compound

The present disclosure firstly provides a compound of formula (I):

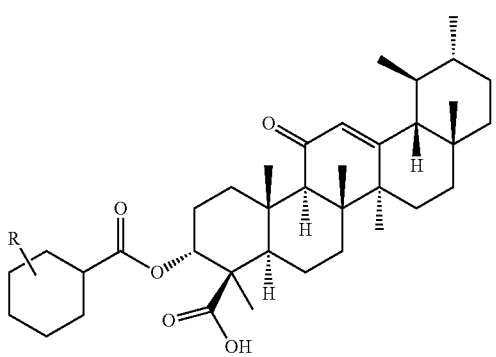

(I)

wherein R is independently selected from the group consisting of H, OH, C1-C4 alkyl, C2-C4 alkenyl, C2-X4 alkynyl and halogen. Preferably, R is independently selected from the group consisting of H, OH and C1-C2 alkyl.

The present disclosure also includes the isomer solvate or precursor or pharmaceutically acceptable salt of the compound of formula (I), as long as they exhibit an identical or a basically identical function to the compound of formula (I). The "pharmaceutically acceptable salt" refers to the salt formed by reaction between a compound and an inorganic acid, organic acid, alkali metal or alkali earth metal, etc. These salts include but are not limited to (1) salts formed with the following inorganic acid, such as hydrochloric acid, sulphuric acid, nitric acid, phosphoric acid; (2) salts formed with the following organic acid, such as acetic acid, oxalic acid, succinic acid, tartaric acid, methanesulfonic acid, maleic acid, or arginine. Other salts include salts formed with alkali metal or alkali earth metal, such as sodium, potassium, calcium or magnesium, in a form of ester, carbamate or other common "prodrug". Compound may have one or more asymmetric centers. As such, these compounds may be present in a form of a racemic mixture, individual enantiomer, individual diastereoisomer, a mixture of diastereoisomers, or cis-isomer or trans-isomer.

The "precursor of the compound" refers to that the precursor is metabolized or converted in vivo in a patient by a chemical reaction into a compound of formula (I) or into a salt or solution consisting of a compound of formula (I), after administered by a suitable method.

As a preferred embodiment of the present disclosure, the compound is shown in the following formula (II):

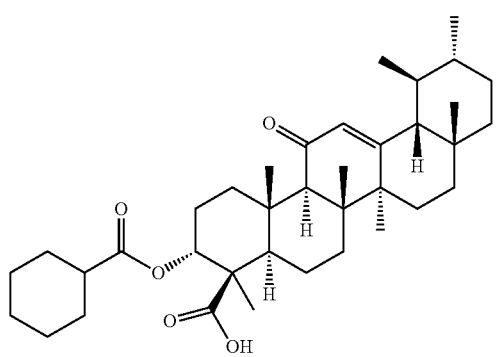

(II)

which is 3-o-α-cyclohexanoyl-11-keto-β-boswellic acid (CKBA).

It should be understood that after knowing the structure of the compound of the present disclosure, the skilled artisan can produce the compounds via various methods and materials known in the art. For example, the methods may include a chemical synthesis method or a method by extracting from organism, such as animal or plant, all of which are contained in the present disclosure.

As a preferred embodiment of the present disclosure, a method for preparing the compound of formula (I) is provided, comprising replacing the AcO group of the starting material, acetyl-11-keto-β-boswellic acid, with group

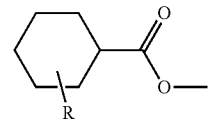

More preferably, the preparation steps include: (i) reacting the starting material, acetyl-11-keto-β-boswellic acid (AKBA), with a base such as KOH to produce 11-keto-β-boswellic acid; and (ii) reacting the 11-keto-β-boswellic acid with cyclohexanecarboxylic acid chloride to produce the compound of formula (I). Other methods for preparing the compound of formula (I) are also contemplated. For example, 11-keto-β-boswellic acid (KBA) may be used as a starting material to react with cyclohexanecarboxylic acid chloride to directly produce the compound of formula (I).

The synthesized compound may be further purified by column chromatography or high performance liquid chromatography, etc.

Use

The inventors found during the study that the compound of formula (I) of the present disclosure could more significantly inhibit cell division and proliferation and exhibited a more significant efficacy on the treatment of psoriasis. Additionally, the compound of formula (I) of the present invention could obviously inhibit activation of NF-kappa B and exhibits a more ideal efficacy than AKBA.

For example, many molecules involved in the early stage of immune response and in various stages of inflammatory response are modulated by NF-κB, including TNF-α, IL-1β, IL-2, IL-6, IL-8, IL-12, iNOS, COX2, chemokines, adhesion molecules, and colony stimulating factor, etc. Additionally, molecules involved in anti-inflammation and apoptosis, such as zinc finger protein A20, heme oxygenase-1 (HO-1), tumour-necrosis factor receptor associated factor-1 (TRAF-1), inhibitor of apoptosis 1 (IAP1), inhibitor of apoptosis 2 (IAP2), TNF receptor-associated factors (TRAF1/TRAF2), Bcl-2 homology A1/Bfl-1, and IEX-IL are also modulated by NF-κB.

Based on the new discovery of the inventors, the present disclosure provides use of the compound of formula (I), or isomer, solvate or precursor or pharmaceutically acceptable salt thereof in the manufacture of a medicament for treating $T_H1$- or $T_H17$-mediated autoimmune diseases, or for treating psoriasis. The $T_H1$- or $T_H17$-mediated autoimmune diseases include but are not limited to psoriasis, such as rheumatoid arthritis, lupus erythematosus, chronic enteritis, multiple cerebral sclerosis, etc.

Pharmaceutical Composition

The present disclosure also provides a pharmaceutical composition, comprising (a) an effective amount of a compound of formula (I), or isomer, solvate or precursor or pharmaceutically acceptable salt thereof; and (b) a pharmaceutically acceptable carrier or excipient.

In the present disclosure, the pharmaceutical composition comprises 0.01-5 wt % of a compound of formula (I) or its pharmaceutically acceptable salt. Preferably, the pharmaceutical composition comprises 0.03-3 wt % of a compound of formula (I) or its pharmaceutically acceptable salt. More preferably, pharmaceutical composition comprises 0.05-1 wt % of a compound of formula (I) or its pharmaceutically acceptable salt.

The present pharmaceutical composition may be present in various dosage forms, as long as the active ingredient could effectively reach the mammal body. For example, the dosage form may be selected from gel, aerosol, tablet, capsule, powder, granule, syrup, solution, or suspension. Dosage form convenient for use could be selected by the skilled artisan according to the diseases to be treated by the compound of the present disclosure.

For ease of preparation and administration, the pharmaceutical composition preferably is a solid composition, especially a tablet, and capsule filled with solid or liquid. The compound or pharmaceutical composition of the present invention may be stored in a sterilized instrument suitable for injection or infusion.

When the pharmaceutical composition is used for treating psoriasis, it is preferred that the composition is topically administered. Various pharmaceutical carriers suitable for formulating a topical formulation could be used in the present disclosure. As a preferred embodiment, the pharmaceutically acceptable carrier includes glycerol, propylene glycol, Carbomer and/or triethanolamine.

As a preferred embodiment of the present disclosure, steps for preparing a topical gel composition comprise adding an effective amount of a compound of formula (I) into a container and then adding anhydrous ethanol to thoroughly dissolve the compound of formula (I); adding a prescribed amount of Carbomer into a suitable amount of water and placing overnight to allow sufficient swelling; mixing prescribed amounts of glycerol, propylene glycol, the swollen Carbomer and preservative with the dissolved compound of formula (I) and stirring until a uniform mixture is obtained; and adjusting the pH of the mixture with triethanolamine to make the pH value of the composition to be 5.8. As demonstrated by the animal test, after treated with the topical gel formulation of the compound of formula (I), the sick skin of the psoriasis patient obviously becomes normal and the inflammatory cells within skin dermis are obviously reduced.

The effective administration dose of the compound of formula (I) as active ingredient may vary depending on the administration mode and the severity of the disease to be treated. However, generally, satisfactory results could be obtained when the compound of the present disclosure is administered in a dose of about 5-500 mg/kg of body weight of animal, preferably 10-300 mg/kg of body weight of animal, more preferably 20-200 mg/kg of body weight of animal, most preferably 50-75 mg/kg of body weight of animal. Preferably, the dose is divided for administration for 1 to 3 times per day, or the compound is administered in a sustained-release form. The dosing regimen may be adjusted to provide the best treatment response. For example, several individual doses may be administered daily or the dose may be proportionally reduced according to the urgency of the treatment status.

The present invention will be further illustrated in connection with the following specific examples. It should be understood that these examples are merely for illustrating the present invention but not for limiting the scope of the present invention. Methods of experiment with their specific conditions being not specified in the following examples are carried out according to the conventional conditions or according to the conditions recommended by the manufacturer. Unless otherwise indicated, all percentages and parts are calculated based on weight.

EXAMPLE 1

Preparation and Identification of Compound of Formula(II)

8 g of acetyl-11-keto-β-boswellic acid (AKBA) and 2.63 g KOH were added into a 100-mL two-neck flask. 50 mL isopropanol used as solvent were added under nitrogen protection. The mixture was refluxed under heating for about 6 hours and then the reaction system was allowed to cool to room temperature. Then the solvent was evaporated by a rotary evaporator to produce a white solid. 30 mL dichloromethane were added to the solid and then diluted hydrochloric acid was added to adjust the pH value of the mixed system to be acidic. The water phase was extracted by dichloromethane for 3 times (3*15 mL). The dichloromethane solvent was collected and dried by anhydrous magnesium sulfate. The solvent was evaporated to produce a brown oily product. The brown oily product was purified by column chromatography by using petroleum ether: ethyl acetate (90:10) as an eluent to obtain 5.8 g KBA as a white solid, with a yield of about 78%. 1 g KBA was dissolved in 10 mL dichloromethane (contained 2 mol % 4-dimethylpyridine). 1.5 eq Triethylamine and 1.2 eq cyclohexanecarboxylic acid chloride were added and the mixture was placed in an ice bath overnight. After completion of reaction, the mixture was treated by 10% sodium bicarbonate solution, and then extracted by dichloromethane for 3 times (3*10 mL). The dichloromethane solvent was collected and dried by anhydrous magnesium sulfate. The solvent was evaporated to produce a white solid. The white solid was purified by column chromatography by using petroleum ether: ethyl acetate (90:10) as an eluent to obtain the acetylated product 3-o-α-cyclohexanoyl-11-keto-β-boswellic acid (yield, about 55%).

An amount of compound of formula (II) was subjected to nuclear magnetic resonance and mass spectrum, indicating that the molecular formula of the compound of formula (II) is $C_{37}H_{56}O_5$ with a molecular weight of 581, as evidenced in FIGS. 1-4.

EXAMPLE 2

Preparation of Gel of Compound of Formula (II)

(1) Gel 1

An amount of formula (II) compound was weighed and formulated to 100 g gels according to the following formulations: 0.2 g compound of formula (II); 2 g glycerol; 2 g propylene glycol; 1.5 g Carbomer; 2.5 mL anhydrous ethanol; 0.5 g preservative (SupGuard GM-BP, general compound antibacterial agent); and water; to 100 g. The compound of formula (II) was dissolved in the anhydrous ethanol firstly, and Carbomer was swelled in water overnight. The above components were mixed and stirred and then triethanolamine was used to adjust the pH to 5.8. The resultant gel 1 contained 0.2% (w/w) of the compound of formula (II).

(2) Gel 2

An amount of formula (II) compound was weighed and formulated to 100 g gels according to the following formulations: 0.5 g compound of formula (II); 2 g glycerol; 2 g propylene glycol; 1.5 g Carbomer; 2.5 mL anhydrous ethanol; 0.5 g preservative; and water; to 100 g. The compound of formula (II) was dissolved in the anhydrous ethanol firstly, and Carbomer was swelled in water overnight. The above components were mixed and stirred and then triethanolamine was used to adjust the pH to 6.0. The resultant gel 2 contained 0.5% (w/w) of the compound of formula (II).

(3) Gel 3

An amount of formula (II) compound was weighed and formulated to 100 g gels according to the following formulations: 0.1 g compound of formula (II); 2 g glycerol; 2 g propylene glycol; 1.5 g Carbomer; 2.5 mL anhydrous ethanol; 0.5 g preservative; and water; to 100 g. The compound of formula (II) was dissolved in the anhydrous ethanol firstly, and Carbomer was swelled in water overnight. The above components were mixed and stirred and then triethanolamine was used to adjust the pH to 5.9. The resultant gel 3 contained 0.1% (w/w) of the compound of formula (II).

(4) Gel 4

An amount of formula (II) compound was weighed and formulated to 100 g gels according to the following formulations: 1 g compound of formula (II); 2 g glycerol; 2 g propylene glycol; 1.5 g Carbomer; 2.5 mL anhydrous ethanol; 0.5 g preservative; and water; to 100 g. The compound of formula (II) was dissolved in the anhydrous ethanol firstly, and Carbomer was swelled in water overnight. The above components were mixed and stirred and then triethanolamine was used to adjust the pH to 6.0. The resultant gel 4 contained 1% (w/w) of the compound of formula (II).

(5) Blank Gel

100 Grams gel contained 2 g glycerol; 2 g propylene glycol; 1.5 g Carbomer; 2.5 mL anhydrous ethanol; 0.5 g preservative; and water; to 100 g. The compound of formula (II) was dissolved in the anhydrous ethanol firstly, and Carbomer was swelled in water overnight. The above components were mixed and stirred and then triethanolamine was used to adjust the pH to 6.0. The resultant blank gel was used as a control in the animal test.

EXAMPLE 3

In vitro Inhibition of Growth of Skin Keratinocyte

HaCat keratinocytes (purchased from ATCC) in a logarithmic growth phase were inoculated in a 96-well plate, with $2\times10^4$ cells for each well. The compound of formula (II) and AKBA were added respectively in a concentration gradient. The total volume was 100 mL. DMSO was added in the control group to a final concentration of 0.25%. 100 mL culture medium was added into the blank control well. Each group had three parallel experiments. After cultured in a cell incubator for 24 hours, 10 mL CCK-8 solution was added into each well. Then the plate was placed in the incubator for incubation at 37° C. and 5% $CO_2$ for 4 hours. OD value was measured at 450 nm by a microplate reader. The inhibition rate was calculated by the following equation: Inhibition Rate=[1−(OD of the test group/OD of the control group)]×100%.

Figure 5:
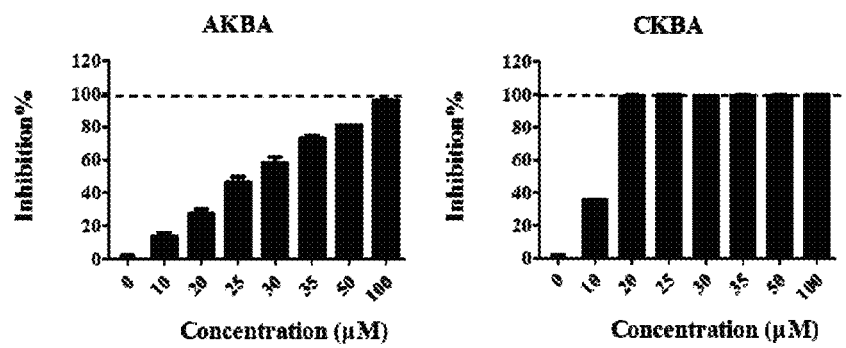
FIG. 5: Experiments about inhibition of different concentrations of formula (II) compound (CKBA) and AKBA on the growth of skin keratinocytes, indicating that the formula (II) compound is more effective than AKBA in inhibiting division and proliferation of the skin keratinocytes.

Results were showed in FIG. 5, indicating that the compound of formula (II) (CKBA) was more effective in inhibiting division and proliferation of HaCat cells as compared to AKBA. CKBA could completely inhibit the growth of the skin keratinocyte at a lower concentration (20M), while AKBA produced the same effect at 100 μM. Thus, CKBA exhibited a significant better activity than AKBA.

EXAMPLE 4

Inhibition of In Vitro Differentiation of $T_H1$ and $T_H17$ Cells

C57BL/6J mice of 6-8 week old were sacrificed by cervical vertebra luxation. The spleen was taken and ground. The cells were sieved to prepare a single-cell suspension. After dyeing on their surfaces by CD4-APC, CD25 PerCP-Cy 5.5 and CD62L-FITC, the cells were sorted by BD FACSAria III flow cytometry. The naïve T cells, i.e., $CD4^+ CD25^- CD62L^{hi+}$ T cells, were used for induced differentiation of $T_H1$, $T_H17$ and $T_{reg}$. A gradient of concentration of CKBA was added for incubation. Cells were collected after 4 days and then further cultured in incubator at 37° C. and 5% $CO_2$ for 4-6 hours in 1640 complete culture medium supplemented with 750 ng/ml ionomycin and 50 ng/ml phorbol myristate acetate (PMA) and GolgiPlug. After suspension with PBS, the surface of the cell was stained by CD4-APC. After staining at 4° C. for 30 minutes, the cells were re-suspended once and then broke for 20 minutes at 4□. The cells were washed again by lotion and then stained by IFN-γ, IL-17A and FoxP3.

Figure 6:
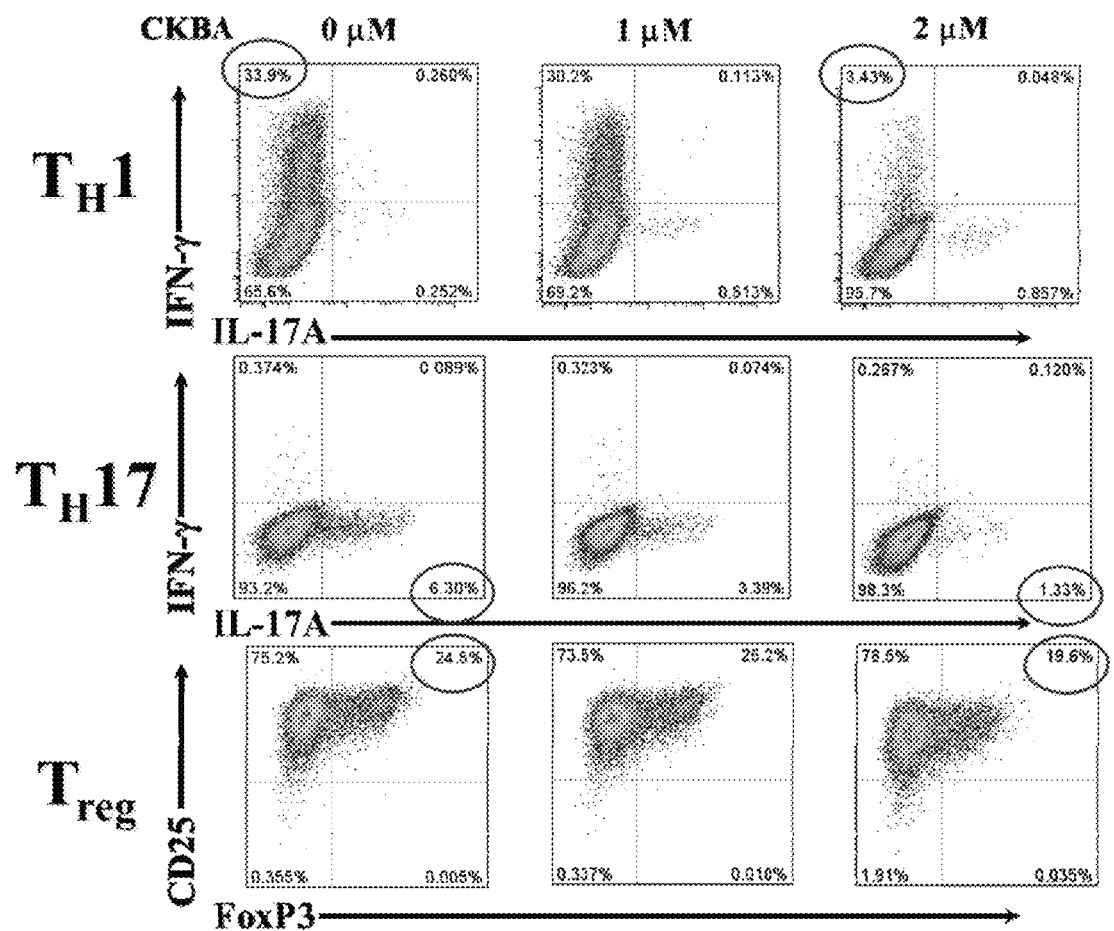
FIG. 6: Experiments about inhibition of the formula (II) compound on in vitro differentiation of the $T_H1$ and $T_H17$ cells.

As analyzed by flow cytometry, results showed that 2 μm of CKBA could very effectively inhibit in vitro differentiation of $T_H1$ and $T_H17$, while exhibited no inhibition on differentiation of $T_{reg}$, as shown in FIG. 6.

EXAMPLE 5

In Vivo Inhibition of NF-Kappa B by Gel Formulation

Twenty age- and sex-matched Balb/c mice, 10 in the control group using a blank gel and 10 in the treatment group using CKBA gel (Gel 2 in Example 2, containing 0.5% (w/w) of the compound of formula (II)) were coated on their backs by imiquimod (62.5 mg/day for each mouse) for 7 days to establish mouse psoriasis model. At day 8, the blank gel (Control) and CKBA gel were coated on the backs of the mice. Skins were taken from the skin lesion at day 9 (24 hours after treatment) and day 10 (48 hours after treatment) for extraction of protein, where was then analyzed by Western Blotting.

Figure 7:
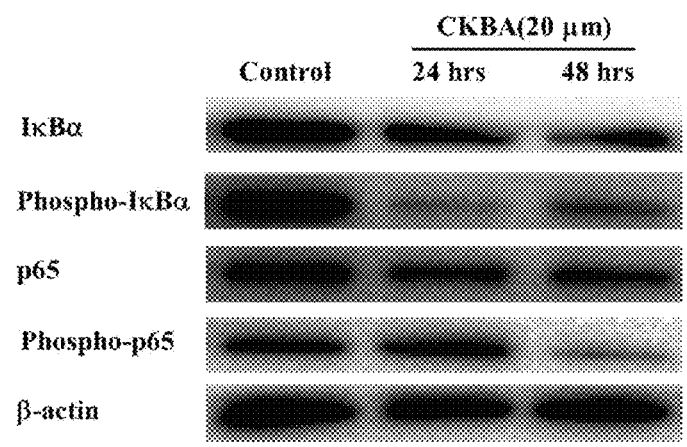
FIG. 7: The formula (II) compound inhibits activation of NF-kappa B.

Phosphorylated IκBα (Phospho-IκB) and Phosphorylated p65 (Phospho-p65) were analyzed. Results showed that CKBA gel (0.5% (w/w) of the compound of formula (II)) significantly reduced the production of Phospho-IκB and Phospho-p65 as compared to the control group, thus it could effectively inhibit activation of NF-kappa B at the skin lesion of the psoriasis mice, as shown in FIG. 7.

EXAMPLE 6

Figure 8:
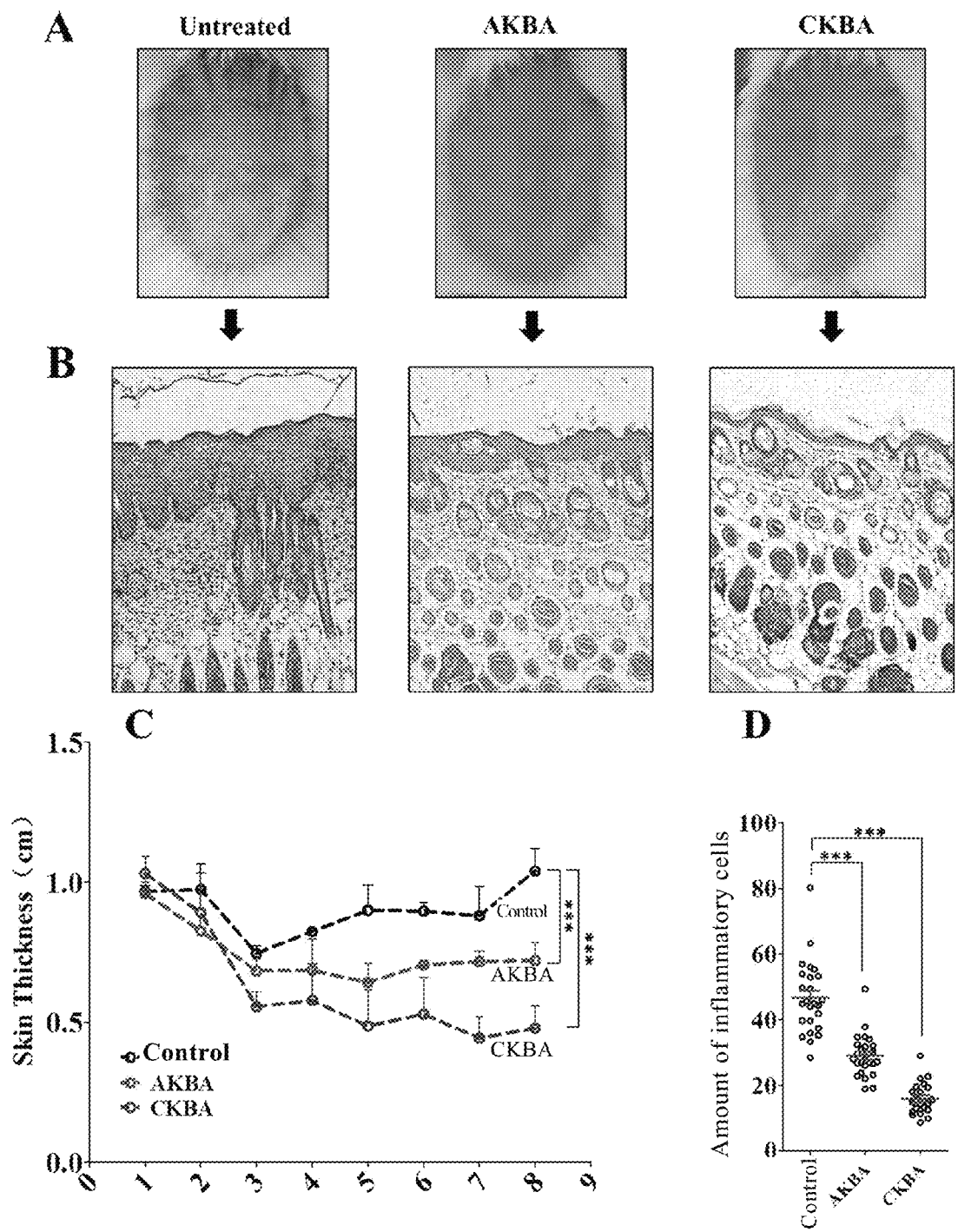
FIG. 8: Mice suffering from psoriasis were treated with a gel containing 0.5% (w/w) of the formula (II) compound (CKBA) or a gel containing 0.5% (w/w) of AKBA. The results showed that the symptom of mice suffering from psoriasis treated by CKBA is significantly improved than mice treated with AKBA of the same concentration.
A. Mice suffering from psoriasis induced by Imiquimod were treated by control (a gel without AKBA or CKBA), AKBA gel or CKBA gel for 4 times, respectively;
B. HE photos of the skin lesions of mice suffering from psoriasis induced by Imiquimod treated by control, AKBA gel or CKBA gel for 4 times, respectively;
C. Skin thickness of the skin lesions of mice suffering from psoriasis induced by Imiquimod treated by control, AKBA gel or CKBA gel for 4 times, respectively;
D. Amount of inflammatory cells in dermis of the skin lesions of mice suffering from psoriasis induced by Imiquimod treated by control, AKBA gel or CKBA gel for 4 times, respectively (Amount of inflammatory cells/HPF (high power field)).

Treatment of Mice Psoriasis by Gel Formulation Containing 0.5% (w/w) Active Ingredient Thirty age- and sex-matched Balb/c mice, 10 in the control group using a blank gel, 10 in the treatment group using AKBA gel and 10 in the treatment group using CKBA gel, were coated on their backs by imiquimod (62.5 mg/day for each mouse) for 7 days to establish mouse psoriasis model. At day 8 to day 14, the blank gel (Control), AKBA gel (0.5% (w/w)) and CKBA gel (0.5% (w/w)) were administered to the mice for treatment, respectively. Imiquimod was administered every two days to the back of the mice to maintain the skin inflammation. At day 15 pictures were took for the skin lesions of the psoriasis mice. Then the mice were sacrificed by cervical vertebra luxation and the skin from the skin lesion was cut and fixed by 4% paraformaldehyde to prepare HE pathological sections. According to the observations on the area of epidermis and the inflammatory cells in dermis from the disease phenotype and the pathological sections, it could conclude that both the compound of formula (II) (CKBA) (0.5% (w/w)) and AKBA (0.5% (w/w)) could effectively relieve the mice psoriasis phenotype (FIGS. 8A and 8B) and significantly reduce the skin thickness (FIG. 8C) and the number of the inflammatory cells (FIG. 8D). Moreover, as compared to AKBA the compound of formula (II) (CKBA) could more effectively treat mice psoriasis with a more ideal treatment effect.

EXAMPLE 7

Treatment of Mice Psoriasis by Gel Formulation Containing 0.2% (w/w) Active Ingredient Thirty age- and sex-matched Balb/c mice, 10 in the control group using a blank gel, 10 in the treatment group using AKBA gel and 10 in the treatment group using CKBA gel, were coated on their backs by imiquimod (62.5 mg/day for each mouse) for 7 days to establish mouse psoriasis model. At day 8 to day 14, the blank gel (Control), AKBA gel (0.2% (w/w)) and CKBA gel (0.2% (w/w)) were administered to the mice for treatment, respectively. Imiquimod was administered every two days to the back of the mice to maintain the skin inflammation. At day 15 pictures were took for the skin lesions of the psoriasis mice. Then the mice were sacrificed by cervical vertebra luxation and the skin from the skin lesion was cut and fixed by 4% paraformaldehyde to prepare HE pathological sections.

Figure 9:
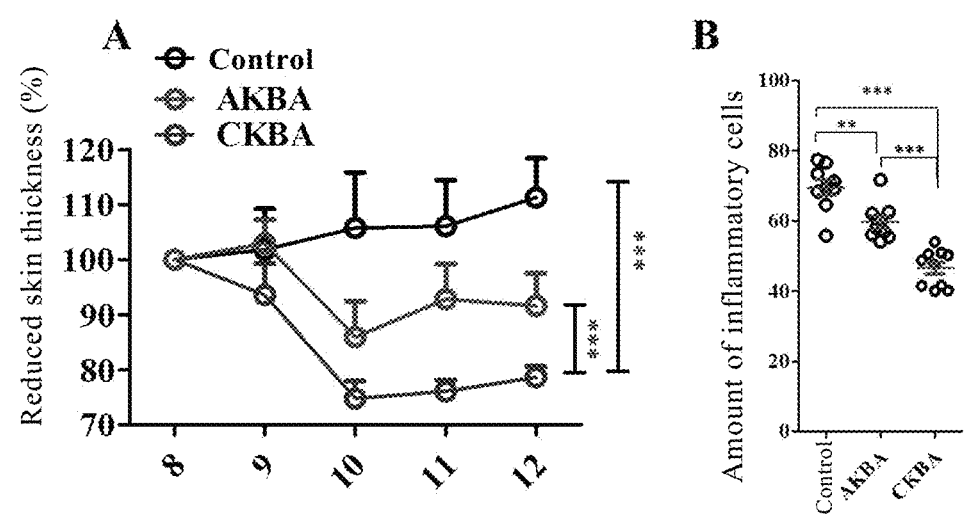
FIG. 9: Experiments by using a gel containing 0.2% (w/w) of the formula (II) compound to treat mouse psoriasis. The results showed that 0.2% (w/w) of the formula (II) compound could effectively treat the psoriasis of mouse.
A. Skin thickness of the skin lesions of mice suffering from psoriasis induced by Imiquimod treated by control or CKBA gel, in which the ordinate indicates the percentage of the reduced thickness;
B. Amount of inflammatory cells in dermis of the skin lesions of mice suffering from psoriasis induced by Imiquimod treated by control or CKBA gel (Amount of inflammatory cells/HPF (high power field)).

According to the observations on the area of epidermis and the inflammatory cells in dermis from the disease phenotype and the pathological sections, it could conclude that the compound of formula (II) (CKBA) (0.2% (w/w)) could effectively cure the mice psoriasis and significantly reduce the skin thickness and the number of the inflammatory cells, as shown in FIG. 9.

The above examples are used for illustrating the technical concept and characteristic of the present invention to allow the skilled artisan to understand the content of the present invention and to practice the invention. They are not used for limiting the protection scope of the present invention. Any equivalent modification or change within the spirit of the present invention should fall within the protection scope of the present invention.

The invention claimed is:

1. A compound of formula (I), an isomer, a solvate, or a pharmaceutically acceptable salt thereof:

(I)

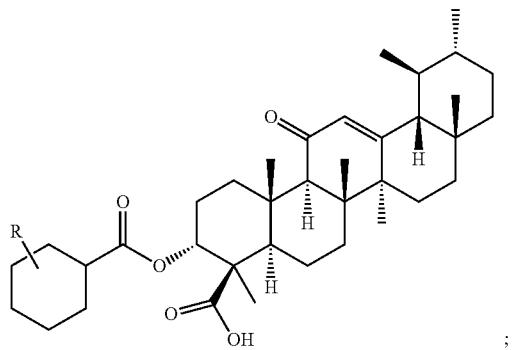

wherein R is independently selected from the group consisting of H, OH, C1-C4 alkyl, C2-C4 alkenyl, C2-C4 alkynyl and halogen.

2. The compound of formula (I), isomer, solvate, or pharmaceutically acceptable salt thereof of claim 1, wherein R is independently selected from the group consisting of H, OH and C1-C2 alkyl.

3. The compound of formula (I), isomer, solvate, or pharmaceutically acceptable salt thereof of claim 1, wherein R is H.

4. A method for preparing the compound of formula (I) according to claim 1:
wherein the method comprises replacing the $CH_3C(O)O$ group of the starting material, acetyl-11-keto-β-boswellic acid, with the following group:

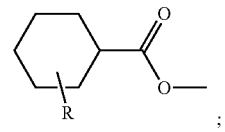

;

wherein the method comprises the following steps:
(i) reacting the starting material, acetyl-11-keto-β-boswellic acid, with a base to produce 11-keto-β-boswellic acid; and
(ii) reacting the 11-keto-β-boswellic acid with cyclohexanecarboxylic acid chloride to produce the compound of formula (I).

5. A pharmaceutical composition for treating psoriasis, comprising: the compound of formula (I), isomer, solvate, or pharmaceutically acceptable salt thereof according to claim 1 and a pharmaceutically acceptable carrier.

6. The pharmaceutical composition of claim 5, wherein the compound of formula (I), isomer, solvate, or pharmaceutically acceptable salt thereof is present in the pharmaceutical composition in an effective amount wherein the effective amount is 0.01-5 wt %, 0.03-3 wt %, or 0.05-1 wt %.

7. The pharmaceutical composition of claim 5, wherein the pharmaceutical composition is a topical formulation, and the pharmaceutically acceptable carrier includes glycerol, propylene glycol, Carbomer, or triethanolamine.

8. A method for treating psoriasis, comprising administering a subject in need thereof an effective amount of the compound of formula (I), isomer, solvate, or pharmaceutically acceptable salt thereof according to claim 1.

9. A pharmaceutical composition for treating psoriasis, comprising: the compound of claim 2, isomer, solvate, or pharmaceutically acceptable salt thereof; and a pharmaceutically acceptable carrier.

10. A pharmaceutical composition for treating psoriasis, comprising: the compound of claim 3, isomer, solvate, or pharmaceutically acceptable salt thereof; and a pharmaceutically acceptable carrier.

11. A method for treating psoriasis, comprising administering a subject in need thereof an effective amount of the compound of claim 2, isomer, solvate, or pharmaceutically acceptable salt thereof.

12. A method for treating psoriasis, comprising administering a subject in need thereof an effective amount of the compound of claim 3, isomer, solvate, or pharmaceutically acceptable salt thereof.

* * * * *